United States Patent [19]

Handte et al.

[11] 4,130,413
[45] Dec. 19, 1978

[54] HETEROCYCLIC PHENYL ETHERS AND HERBICIDES CONTAINING SAME

[75] Inventors: Reinhard Handte, Hofheim am Taunus; Gerhard Hörlein, Frankfurt am Main; Helmut Köcher; Peter Langelüddeke, both of Hofheim am Taunus, all of Fed. Rep. of Germany

[73] Assignee: Hoechst Aktiengesellschaft, Frankfurt am Main, Fed. Rep. of Germany

[21] Appl. No.: 831,480

[22] Filed: Sep. 8, 1977

[30] Foreign Application Priority Data

Sep. 10, 1976 [DE] Fed. Rep. of Germany ....... 2640730

[51] Int. Cl.² ........................................ C07D 277/62
[52] U.S. Cl. .......................................... 71/90; 71/88; 71/92; 548/329; 548/327; 260/307 D; 260/304 B
[58] Field of Search ............................... 71/90, 92, 88; 260/304 B, 307 D; 544/329, 327

[56] References Cited

U.S. PATENT DOCUMENTS

| | | | |
|---|---|---|---|
| 3,574,218 | 4/1971 | Hideg et al. | 260/307 D |
| 3,586,670 | 6/1971 | Brenneisen et al. | 260/307 D |
| 3,840,550 | 10/1974 | Brenneisen et al. | 260/307 D |

*Primary Examiner*—Nicholas S. Rizzo
*Attorney, Agent, or Firm*—Curtis, Morris & Safford

[57] ABSTRACT

Compounds of the formula

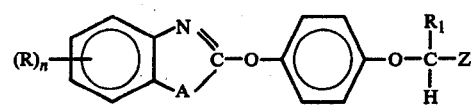

in which
(R)$_n$ is hydrogen, halogen, CF$_3$, NO$_2$, CN, alkyl, alkoxy or alkylthio,
A is O, S, NH, or N-alkyl,
R$_1$ is hydrogen or alkyl and
Z is a carboxylic acid, carboxylic ester, thiol ester, carbonamide, carbohydrazide, thioamide, nitrile, hydroxymethyl, acyloxymethyl, carbamoylmethyl, or sulfonyloxymethyl group, are valuable herbicides for the selective control of weed grasses. The novel compounds are prepared by known methods, for example by reacting halo-benzthiazoles, -benzoxazoles or -benzimidazoles with unilaterally etherified hydroquinones.

15 Claims, No Drawings

HETEROCYCLIC PHENYL ETHERS AND HERBICIDES CONTAINING SAME

This invention provides novel heterocyclically substituted 4-oxyphenoxy-alkane-carboxylic acid derivatives of the formula

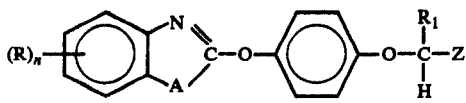

in which
R is halogen, $CF_3$, $NO_2$, CN, $C_1-C_4$alkyl, $C_1-C_4$alkoxy or $C_1-C_4$alkylthio,
A is O, S, NH, or $N-(C_1-C_4)$alkyl,
$R_1$ is H or $C_1-C_4$alkyl,
Z is a group of the formula

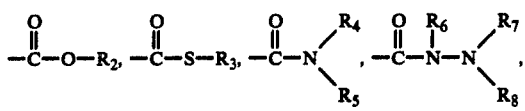

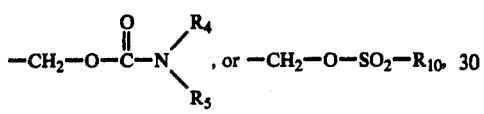

n is zero or 1 or 2,
$R_2$ is H, $C_1-C_{12}$alkyl (optionally substituted by 1 to 6 halogen atoms, preferably F, Cl, Br and/or by OH, $C_1-C_6$alkoxy, $C_1-C_4$alkylthio, $C_1-C_6$alkoxy-$C_2-C_6$alkoxy, halo-$C_1-C_2$alkoxy, methoxyethoxy, $C_1-C_4$alkylamino, di-$C_1-C_4$alkylamino, phenyl, oxiranyl and/or phenoxy which latter may be substituted once or twice by halogen or $C_1-C_4$alkyl); $C_5-C_6$cycloalkyl (optionally substituted by halogen or methyl); $C_3-C_6$alkenyl, halo-$C_3-C_6$alkenyl or $C_5-C_6$cycloalkenyl, $C_3-C_4$alkinyl (optionally substituted once or twice by $C_1-C_6$alkyl, phenyl, halogen or $C_1-C_2$ alkoxy); phenyl (optionally substituted one to three times by $C_1-C_4$alkyl, $C_1-C_4$alkoxy, halogen, $NO_2$, or $CF_3$); furfuryl, tetrahydrofurfuryl, or the cation equivalent of an organic or inorganic base;
$R_3$ is $C_1-C_6$alkyl, phenyl-$(C_1-C_2)$-alkyl, the phenyl radical optionally being substituted once or twice by $C_1-C_4$alkyl and/or halogen, $C_3-C_6$alkenyl, or phenyl (optionally substituted once or twice by $C_1-C_4$alkyl and/or halogen)
$R_4$ and $R_5$, which are identical or different, are H, $C_1-C_6$alkyl, hydroxy-$(C_1-C_6)$-alkyl, $C_5-C_6$cycloalkyl, or phenyl (optionally substituted one to three times by $C_1-C_4$alkyl, $C_1-C_4$alkoxy, halogen or $CF_3$), with the proviso that $R_4$ and $R_5$ cannot be phenyl at the same time; or wherein $R_4$ and $R_5$ together form a methylene chain having 2,4 or 5 $CH_2$-groups in which one $CH_2$ group may be replaced by O, NH, or $N(CH_3)$;
$R_6$ is H or $CH_3$,
$R_7$ is H, $CH_3$, or $C_2H_5$,
$R_8$ is H, $CH_3$, $C_3H_5$ or phenyl,
$R_9$ is $C_1-C_6$alkyl (optionally substituted one to three times by halogen), cyclopropyl, $C_3-C_6$alkenyl, phenyl, $C_1-C_4$alkylphenyl $C_1-C_4$alkoxyphenyl, halophenyl, trifluoromethylphenyl or nitrophenyl and
$R_{10}$ is $C_1-C_4$alkyl or phenyl (optionally substituted once or twice by halogen, $CF_3$, $NO_2$, $C_1-C_4$alkyl).

The alkyl, alkenyl and alkinyl radicals in $R_1$ to $R_5$, $R_9$ and $R_{10}$ may have straight or branched chains.

Preferred compounds of formula I are those in which
R is halogen, $CF_3$, $NO_2$, $CH_3$, methoxy;
A is O, S, $N-CH_3$;
$R_1$ is H, $CH_3$ and Z has the indicated meaning.
Halogen preferably stands for fluorine, chlorine or bromine.

Among the groups mentioned for Z the following are especially preferred:

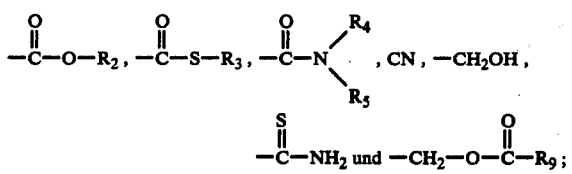

compounds in which Z is

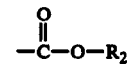

or $-CH_2OH$ being particularly preferred because of their high biological activity.

The compounds of formula I can be prepared by known methods from starting materials known per se, for example
(a) by reacting compounds of formula II

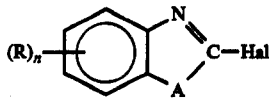

with compounds of formula III

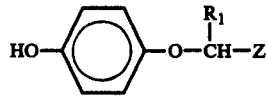

(b) by reacting compounds of formula IV

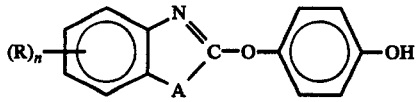

with compounds of formula V

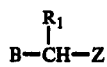

in which B is halogen or a sulfonic ester group, for example a mesyl or tosyl group;
(c) by hydrogenating compounds of formula I in which Z is $-COOR_2$ and optionally transforming the alcohols obtained (Z = $CH_2OH$) into the corresponding carboxylic acid esters (Z = CH$_2$—O—C(O)—R$_9$) by reacting them with carboxylic acids, carboxylic halides or anhydrides; into sulfonic acid esters (Z = CH$_2$O—SO$_2$R$_{10}$) by reacting them with sulfonic acid halides, or into carbamic acid esters

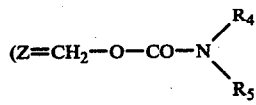

by reacting them with carbamic acid halides or isocyanates; or (d) by transforming the compounds obtained according to processes (a) and (b) into other compounds of formula I by saponification salt formation, esterification, transesterification, amidation, dehydration, or hydration, or addition of hydrogen sulfide.

In respect to process embodiments (a) and (b): The reactions are preferably carried out in inert aprotic solvents such as aliphatic or aromatic hydrocarbons, for example, benzene, toluene, xylene; acid nitriles, for example acetonitrile or propionitrile; ketones, for example acetone, methylethyl ketone, or methylisobutyl ketone; acid amides, for example dimethylformamide, dimethylacetamide, N-methylpyrrolidone, or hexamethyl phosphoric acid triamide, or dimethylsulfoxide, at temperatures from 30° to 250° C. or at the boiling point of the solvent used, preferably at 60° to 160° C., in the presence of inorganic or organic bases, for example metal alcoholates, tertiary amines, alkali metals or alkaline earth metal carbonates and hydroxides such as NaOh and KOH.

As to (c): The reduction of acids or esters to the alcohols is preferably effected with complex metal hydrides such as LiAlH$_4$ in ethereal, anhydrous solvents. Owing to the fact that the reaction generally proceeds exothermally, outside heating is usually unnecessary. The subsequent esterification with acid anhydrides or acid halides is carried out in inert solvents (as in process a) at temperatures of from 0° C. to the boiling point of the solvent with the addition of an organic or inorganic base, for example Na$_2$CO$_3$, K$_2$CO$_3$, pyridine, or triethyl amine. Esterification of the alcohols with carboxylic acids is brought about by adding an acid-binding agent such as P$_2$O$_5$ or by azeotropic extractive distillation of the acidified components. Carbamic acid halides and isocyanates can be reacted within the alcohols in the presence of bases under conditions similar to those used for carboxylic acid halides, generally at slightly higher temperatures, preferably of from 40° C. to the boiling point of the solvent used.

(d): As to for amidating the compounds of formula I esters can be used which are reacted with amines, ammonia, or hydrazines. The solvents used are preferably the same as in process (a) and the temperature applied range from 40° C. to reflux temperature. Alternatively, the acids of formula I can first be transformed into the acid halides which are then reacted with ammonia, amines or hydrazines. To bind the hydrogen halide set free an at least equimolar excess of the base used is required. By reacting the acid chloride with alcohols or mercaptans other esters or thioesters of formula I can be prepared.

The transesterification is performed by acid or base catalysis. The alcohol component to be reacted with the ester is preferably added in excess and the lower boiling alcohol set free is continually distilled off at the same rate as it is formed in the transesterification process.

The dehydration of amides to obtain nitriles is preferably carried out in aromatic hydrocarbons at temperatures of from 50° C. to the boiling point. The subsequent addition of H$_2$S is expediently performed in an autoclave in the presence of catalytic amounts of a base, preferably ethanolamine, at temperatures of from 50° to 150° C.

The heterocyclic starting materials of formula II are according to the definition of A, correspondingly substituted 2-halobenzoxazoles, 2-halobenzthiazoles, 2-halo-1-alkyl-benzimidazoles or 2-halobenzimidazoles, which are obtainable by known methods, for example by halogenation of the corresponding 2-mercapto compounds or 2-oxo-compounds. (Cf. C.A. 59, pages 396 et sq; Am. Chem. J. 21, page 111 (1988)).

The phenols of formulae III and IV can be prepared, for example, by unilateral etherification of hydroquinone (cf. J. Org. Chem. 39, page 214 (1974), Soc. 1965, pages 954–73).

When R$_1$ is other than hydrogen the compounds of formula I have an asymmetric center and are generally present in the form of a racemate. The racemates can be separated by usual methods into diastereoisomers. In processes (a) and (b) there may also be used optically active starting compounds of formulae III and V.

The compounds of formula I according to the invention have a strong activity both in pre- and post-emergence application, against a wide range of annular and perennial weed grasses, and simultaneously they are excellently tolerated by dicotyledonous crop plants and some cereals. Consequently, the compounds can be used to selectively combat annual and perennial weed grasses in crops. Weed grasses against which the compounds of the invention are effective are, for example, wild oat (Avena), blackgrass (*Alopecurus spp*), meadow grass (*Poa spp*), raygrass (*Lolium spp*), annual and perennial wild millets (*Echinochloa spp., Setaria spp., Digitaria spp., Panicum spp., Sorghum spp.*), Bermuda grass (*Cynodon spp.*) and couch grass (*Agropyron spp.*).

It is, therefore, another object of the present invention to provide herbicidal compositions containing as active ingredient a herbicidally active amount of a compound of formula I in addition to the usual additives and formulations auxiliaries.

The compounds can therefore be used for the manufacture of herbicidal compositions, which preferably contain 2-95% of the active compounds of the formula (I). They are customarily formulated as wettable powders, emulsifiable concentrates, dusting agents, granules, etc.

Wettable powders are formulations which are uniformly dispersible in water and which, in addition to the active compound, also contain diluents or inert materials, wetting agents, for example, polyoxyethylated alkylphenols, polyoxyethylated oleylamines or stearylamines, alkylsulfonates or alkylphenylsulfonates and dispersing agents, for example sodium ligninsulfonates, sodium 2,2'-dinaphthylmethane-6,6'-disulfonate or the sodium salt of oleyl-methyl-taurine.

Emulsifiable concentrates are obtained by dissolving the active compound in an organic solvent, for example butanol, cyclohexanone, dimethylformamide, xylene or even higher-boiling aromatics, and adding a non-ionic wetting agent, for example a polyoxethylated alkylphenol or a polyoxyethylated oleylamine or stearylamine.

Dusting agents are obtained by grinding the active compound with finely divided solids, for example, talc, natural clays, such as kaolin, bentonite pyrophillite or diatomaceous earth.

Granules can be manufactured either by spraying the active compound onto adsorbent, granular inert material or by applying active compound concentrates by means of adhesives, for example polyvinyl alcohol, sodium polyacrylate or even mineral oils, onto the surfaces of carriers, such as sand, kaolinites or granular inert material. Suitable formulations can also be manufactured by the customary methods of manufacture of fertilizer granules, if desired in admixture with fertilizers.

In the case of herbicidal compositions, the concentrations of the active compounds in the commercial formulations can vary. In wettable powders, the active compound concentration varies, for example, between 10% and 95%, the remainder consisting of one or more of the abovementioned formulation additives. In the case of emulsifiable concentrates, the active compound concentration is about 10% to 80%. Dust formulations usually contains 5–20% of active compound. In the case of granules, the active compound content in part depends on whether the active compound is in a liquid or solid form and what granulating auxiliaries, fillers and the like are used.

If necessary or desired the commercial concentrates may be diluted prior to application in the usual manner, for example by means of water in the case of wettable powders and emulsifiable concentrates.

Dusts, granules and sprayable solutions are generally ready for use without further dilution. The amount of active compound necessary for obtaining the desired result depends on external conditions such as temperature, humidity, type of soil, stage of plant development etc. It can vary within wide limits, for example between 0.05 and 10.0 kg/ha of active substance but is preferably between 0.1 and 5 kg/ha.

The active compounds according to the invention can be combined with other herbicides, insecticides and fungicides.

The following examples illustrate the invention.

EXAMPLE A

An emulsifiable concentrate is obtained from
15 parts by weight of active substance
75 parts by weight of cyclohexanone as solvent and
10 parts by weight of oxethylated nonyl phenol (10 EO) as emulsifier.

EXAMPLE B

A wettable powder which is easily dispersible in water is obtained by mixing
25 parts by weight of active substance
64 parts by weight of quartz-containing kaolin as inert material
10 parts by weight of potassium lignosulfonate and
1 part by weight of sodium oleyl-methyl-taurine as wetting and dispersing agent and grinding the mixture in a pin mill.

EXAMPLE C

A dusting powder is obtained by mixing
10 parts by weight of active substance and
90 parts by weight of talc as inert material and comminuting the mixture in a hammer mill.

EXAMPLE D

A granular formulation consists, for example, of about
2 to 15 parts by weight of active substance and
98 to 85 parts by weight of inert granular materials such as attapulgite, pumice and quartz sand.

EXAMPLES OF PREPARATION

EXAMPLE 1

2-[4'-(Benzthiazol-2"-yl-oxy)-phenoxy]-propionic acid ethyl ester

For salt formation 42 g (0.2 mol) of 2-(4'-hydroxy-phenoxy)-propionic acid ethyl ester were refluxed for 90 minutes together with 33.1 g (0.24 mol) of potassium carbonate in 300 ml of acetonitrile. Next, 33.9 g (0.2 mol) of 2-chlorobenzthiazole were added and the mixture was further boiled until no more starting materials could be detected in a thin layer chromatogram (30 hours).

To remove the salt the hot mixture was filtered and the acetonitrile was distilled off. The residue was distilled, whereupon 60.7 g (88.5% of the theory) of 2-[4'-(benzthiazole-2"-yl-oxy)-phenoxy]-propionic acid ethyl ester boiling at 202 to 204° C. under 0.1 bar were obtained.

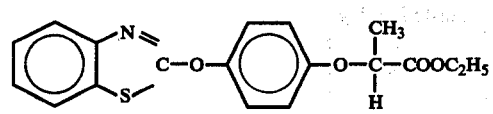

EXAMPLE 2

2-[4'-(benzthiazol-2'-yl-oxy)-phenoxy]-propanol 94 g (0.274 mol) of the ester obtained as described in Example 1 were added to 400 ml of absolute diethyl ether and a suspension of 7.2 (0.19 mol) of lithium-aluminum hydride in 300 ml of absolute ether was added dropwise at a rate such that the reaction mixture boiled. After the addition, the mixture was refluxed for 1 hour. After cooling, 350 ml of water and 400 ml of 2N sulfuric acid were added. The phases were separated and the aqueous phase was shaken three times, each time with 150 ml of diethyl ether. The combined ether extracts were washed with water, dried and evaporated to dryness under reduced pressure. The residue was recrystallized from cyclohexane/toluene. After recrystallization, 75.8 g (92% of the theory) of 2-[4'-(benzthiazole-2"-yl-oxy)-phenoxy]-propanol melting at 102° to 104° C. were obtained.

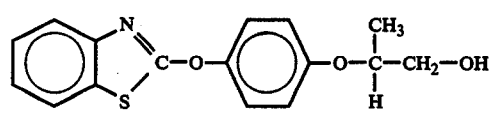

EXAMPLE 3

1-Propylcarbonyloxy-2-[4'-(benzthiazol-2"-yl-oxy)-phenoxy]-propane 20 g (0.07 mol) of the alcohol obtained as described in Example 2 and 8.5 g (0.084 mol) of triethylamine were dissolved in 50 ml of dry toluene and added dropwise over a period of 15 minutes to a solution of 7.3 g (0.08 mol) of butyric acid chloride in 100 ml of dry toluene. After the addition, the mixture was stirred for another 3 hours at 60° C., the triethylamine hydrochloride formed was separated, the filtrate was repeatedly washed with saturated bicarbonate solution and water, dried and evaporated to dryness in a rotary evaporator. The residue was distilled under reduced pressure. After distillation 23 g (88.7% of the theory) of 1-propylcarbonyloxy-2-[4'-benzthiazol-2''-yloxy)-phenoxy]-propane boiling at 207° C. under 0.05 bar were obtained.

(84.8% of the theory) of 1-methylaminocarbonyloxy-2-[4'-(benzthiazol-2''-yl-oxy)-phenoxy]-propane melting at 99° to 100° C. were obtained.

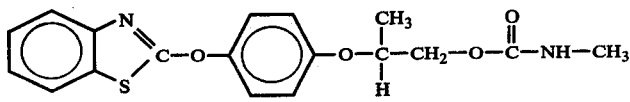

EXAMPLE 5

2-]4'-(5''-CHlorobenzthiazolyl-2''-oxy)-phenoxy]-propionic acid 1-chloroisopropyl ester In a nitrogen atmosphere, 13.9 g (0.05 mol) of 4-(5'-chlorobenzthiazolyl-2'-oxy)-phenol, 8.3 g (0.06 mol) of $K_2CO_3$ and 12.6 g and 12.6 g (0.055 mol) of 2-bromopropionic acid 1-isopropyl ester in 120 ml of methylethyl ketone were stirred for 12 hours at boiling temperature. The salt proportion was filtered off and the solvent removed by distillation. To remove the bromine ester in excess the reaction mixture was dried for 1 hour at 160° C. in a high vacuum. 19.4 g (90.8% of the theory) of 2-[4'-(5''chlorobenzthiazolyl-2''-oxy)-phenoxy]-propionic acid 1-chloroisopropyl ester, $n_D^{26.5} = 1.5900$, were obtained.

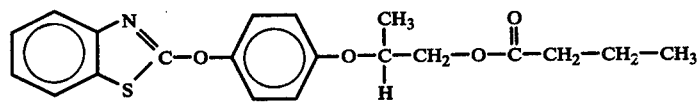

EXAMPLE 4

1-Methylaminocarbonyloxy-2-[4'-(benzthiazol-2''-yl-oxy)-phenoxy]-propane 25 g (0.083 mol) of the alcohol obtained as described in Example 2, 9.5 g (0.166 mol) of methylisocyanate and 1 ml of triethylamine in 150 ml of dry toluene were stirred for 4 hours at 100° C. The reaction mixture was then cooled, washed three times, each time with 150 ml of water, dried and evaporated to dryness in a rotary evaporator. The residue was recrystallized from a water/ethanol mixture. After recrystallization, 25.2 g In a manner analogous to Examples 1 and 5 the following compounds were prepared:

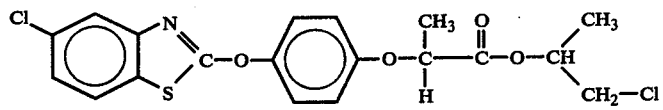

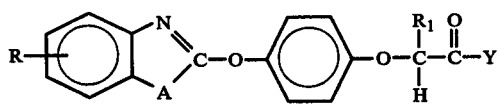

| Example No. | R | A | $R_1$ | Y | m.p./b.p. (° C)/$n_D$ |
|---|---|---|---|---|---|
| 6 | H | S | $CH_3$ | —O—$CH_3$ | m.p. 75.5–76.5 |
| 7 | H | S | $CH_3$ | —O—$C_3H_7(n)$ | $n_D^{25}$: 1.5750 |
| 8 | H | S | $CH_3$ | —O—$C_4H_9(n)$ | $n_D^{25}$: 1.5721 |
| 9 | H | S | $CH_3$ | —O—$CH_2$—$CH(CH_3)_2$ | |
| 10 | H | S | $CH_3$ | —O—$CH_2$—$C_4H_9(n)$ <br> $\|$ <br> $C_2H_5$ | $n_D^{25}$: 1.5543 |
| 11 | H | S | $CH_3$ | —O—⟨H⟩ | $n_D^{25}$: 1.5817 |
| 12 | H | S | $CH_3$ | —O—$CH_2$—CH=$CH_2$ | $n_D^{25.5}$: 1.5896 |
| 13 | H | S | $CH_3$ | —O—$CH_2$—CH=CH—$CH_3$ | |
| 14 | H | S | $CH_3$ | —O—$CH_2$—C≡CH | $n_D^{25}$: 1.5898 |
| 15 | H | S | $CH_3$ | —CH—C≡CH <br> $\|$ <br> $CH_3$ | |
| 16 | H | S | $CH_3$ | —O—$CH_2$—$CH_2$—Cl | $n_D^{25.5}$: 1.5938 |
| 17 | H | S | $CH_3$ | —O—$CH_2$—$CH_2$—$CH_2$—Cl | $n_D^{25.5}$: 1.5868 |
| 18 | H | S | $CH_3$ | —O—CH($CH_2$—Cl)$_2$ | |
| 19 | H | S | $CH_3$ | —O—$CH_2$—$CH_2$—$OCH_3$ | |
| 20 | H | S | $CH_3$ | —O—$CH_2$—$CH_2$—O—$C_4H_9(n)$ | |

-continued

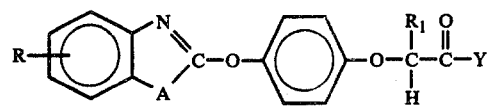

| Example No. | R | A | $R_1$ | Y | m.p./b.p. (° C)/$n_D$ |
|---|---|---|---|---|---|
| 21 | H | S | $CH_3$ | $-O-CH_2-CH_2-\underset{OCH_3}{\overset{H}{C}}-CH_3$ | |
| 22 | 5-$CH_3O$ | S | $CH_3$ | $-O-C_2H_5$ | $n_D^{30}$: 1.5860 |
| 23 | 6-$CH_3O$ | S | $CH_3$ | $-O-C_2H_5$ | $n_D^{30}$: 1.5795 |
| 24 | 5-$CH_3$ | S | $CH_3$ | $-O-C_2H_5$ | m.p. 63.5–66 |
| 25 | 6-$CH_3$ | S | $CH_3$ | $-O-C_2H_5$ | $n_D^{30}$: 1.5814 |
| 26 | 6-$CH_3$ | S | $CH_3$ | $-O-CH_3$ | |
| 27 | 5-$CF_3$ | S | $CH_3$ | $-O-C_2H_5$ | m.p. 66–68 |
| 28 | 5-$CF_3$ | S | $CH_3$ | $-O-CH_3$ | |
| 29 | 5-$CF_3$ | S | $CH_3$ | $-O-C_4H_9(i)$ | |
| 30 | 6-$CF_3$ | S | $CH_3$ | $-O-CH_3$ | |
| 31 | 6-$CF_3$ | S | $CH_3$ | $-O-C_2H_5$ | |
| 32 | 6-$CF_3$ | S | $CH_3$ | $-O-C_4H_9(n)$ | |
| 33 | 6-$NO_2$ | S | $CH_3$ | $-O-C_2H_5$ | m.p. 106.5 |
| 34 | 6-$NO_2$ | S | $CH_3$ | $-O-CH_3$ | |
| 35 | 7-$CH_3$ | S | $CH_3$ | $-O-C_2H_5$ | b.p.$_{0.01}$: 196 |
| 36 | 5-Br | S | $CH_3$ | $-O-CH_3$ | m.p. 86–87 |
| 37 | 5-Br | S | $CH_3$ | $-O-C_2H_5$ | |
| 38 | 5-Br | S | $CH_3$ | $-O-CH_2-CH_2-OCH_3$ | |
| 39 | 5-Cl | S | $CH_3$ | $-CH_3$ | |
| 40 | 5-Cl | S | $CH_3$ | $-O-C_2H_5$ | m.p. 92 |
| 41 | 5-Cl | S | $CH_3$ | $-O-C_6H_{13}(n)$ | $n_D^{25.5}$: 1.5688 |
| 42 | 5-Cl | S | $CH_3$ | $-O-CH_2-\underset{C_2H_5}{CH}-C_4H_9(n)$ | |
| 43 | 5-Cl | S | $CH_3$ | $-O-\langle H \rangle$ | |
| 44 | 5-Cl | S | $CH_3$ | $-O-CH_2-CH_2-Cl$ | |
| 45 | 5-Cl | S | $CH_3$ | $-O-\underset{CH_2Cl}{\overset{H}{\underset{|}{C}}}-CH_3$ | $n_D^{26.5}$: 1.5900 |
| 46 | 5-Cl | S | $CH_3$ | $-CH_2-CH_2-OCH_3$ | |
| 47 | 5-Cl | S | $CH_3$ | $-O-CH_2-CH_2-O-C_4H_9(n)$ | $n_D^{25.5}$: 1.5643 |
| 48 | 5-Cl | S | $CH_3$ | $-O-CH_2-CH=CH_2$ | m.p. 66–67 |
| 49 | 5-Cl | S | $CH_3$ | $-O-CH_2-C\equiv CH$ | m.p. 106.5–108 |
| 50 | 5-Cl | S | $CH_3$ | $-O-\underset{CH_3}{CH}-C\equiv CH$ | |
| 51 | 5-Cl | S | $CH_3$ | $-O-CH_2-CH_2-CH\underset{CH_3}{\overset{OCH_3}{\diagup}}$ | $n_D^{25.5}$: 1.5727 |
| 52 | 6-Br | S | $CH_3$ | $-O-CH_3$ | |
| 53 | 6-Br | S | $CH_3$ | $-O-C_2H_5$ | m.p. 55 |
| 54 | 6-Br | S | $CH_3$ | $-O-CH_2-CH(CH_3)_2$ | |
| 55 | 6-Br | S | $CH_3$ | $-O-CH_2-CH_2-O-C_4H_9(n)$ | |
| 56 | 6-Br | S | $CH_3$ | $-O-CH_2-CH_2-CH_2-Cl$ | |
| 57 | 6-Cl | S | $CH_3$ | $-O-CH_3$ | b.p.$_{0.1}$: 228 |
| 58 | 6-Cl | S | $CH_3$ | $-O-C_2H_5$ | b.p.$_{0.001}$: 204–6 |
| 59 | 6-Cl | S | $CH_3$ | $-O-C_3H_7$ | b.p.$_{0.1}$: 220 |
| 60 | 6-Cl | S | $CH_3$ | $-O-C_3H_7(i)$ | b.p.$_{0.1}$: 215 |
| 61 | 6-Cl | S | $CH_3$ | $-O-C_4H_9(n)$ | b.p.$_{0.4}$: 228–30 |
| 62 | 6-Cl | S | $CH_3$ | $-O-CH_2-CH(CH_3)_2$ | b.p.$_{0.5}$: 255 |
| 63 | 6-Cl | S | $CH_3$ | $-O-C_6H_{13}(n)$ | $n_D^{32}$: 1.5683 |
| 64 | 6-Cl | S | $CH_3$ | $-O-CH_2-\underset{C_2H_5}{CH}-C_4H_9(n)$ | $n_D^{23}$: 1.5656 |
| 65 | 6-Cl | S | $CH_3$ | $-O-\langle H \rangle$ | $n_D^{23}$: 1.5795 |
| 66 | 6-Cl | S | $CH_3$ | $-O-\underset{Cl}{\langle H \rangle}$ | $n_D^{23}$: 1.5856 |
| 67 | 6-Cl | S | $CH_3$ | $-O-CH_2-CH_2-Cl$ | m.p. 88 |
| 68 | 6-Cl | S | $CH_3$ | $-O-CH_2-CH_2-CH_2-Cl$ | m.p. 63 |
| 69 | 6-Cl | S | $CH_3$ | $-O-CH_2-CH_2-CH_2-CH_2-Cl$ | |
| 70 | 6-Cl | S | $CH_3$ | $-O-(CH_2)_6-Cl$ | m.p. 49 |
| 71 | 6-Cl | S | $CH_3$ | $-O-\underset{CH_2Cl}{\overset{CH_3}{\underset{|}{CH}}}$ | $n_D^{23}$: 1.5889 |

-continued

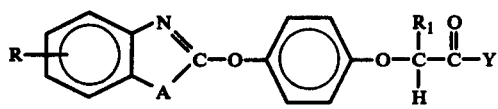

| Example No. | R | A | R₁ | Y | m.p./b.p. (° C)/$n_D$ |
|---|---|---|---|---|---|
| 72 | 6-Cl | S | CH₃ | —O—CH(CH₂—Cl)(CH₂—Cl) | $n_D^{23}$: 1.5940 |
| 73 | 6-Cl | S | CH₃ | —O—CH₂—CHCl—CH₃ | m.p. 59 |
| 74 | 6-Cl | S | CH₃ | —O—CH₂—CBr(H)—CH₃ | |
| 75 | 6-Cl | S | CH₃ | —O—CH₂—CH=CH₂ | m.p. 88 |
| 76 | 6-Cl | S | CH₃ | —O—CH₂—CH=CH—CH₃ | m.p. 44 |
| 77 | 6-Cl | S | CH₃ | —O—CH₂—C≡CH | m.p. 96 |
| 78 | 6-Cl | S | CH₃ | —O—CH(CH₃)—C≡CH | $n_D^{26}$: 1.5912 |
| 79 | 6-Cl | S | CH₃ | —O—CH(C₂H₅)—C≡CH | |
| 80 | 6-Cl | S | CH₃ | —O—C(CH₃)₂—C≡CH | |
| 81 | 6-Cl | S | CH₃ | —O—C(H)(Phenyl)—C≡CH | |
| 82 | 6-Cl | S | CH₃ | —O—CH₂—CH=CH—Br | $n_D^{23}$: 1.6067 |
| 83 | 6-Cl | S | CH₃ | —O—(cyclohexyl-CH₃) | $n_D^{27}$: 1.5786 |
| 84 | 6-Cl | S | CH₃ | —O—(cyclohexyl)—CH₃ | |
| 85 | 6-Cl | S | CH₃ | —O—CH₂—CH₂—OH | |
| 86 | 6-Cl | S | CH₃ | —O—CH₂—CH₂—OCH₃ | $n_D^{23.5}$: 1.5864 |
| 87 | 6-Cl | S | CH₃ | —O—CH₂—CH₂—O—C₂H₅ | |
| 88 | 6-Cl | S | CH₃ | —O—CH₂—CH₂—O—C₄H₉(n) | $n_D^{23}$: 1.5676 |
| 89 | 6-Cl | S | CH₃ | —O—(CH₂—CH₂—O)₂—C₂H₅ | |
| 90 | 6-Cl | S | CH₃ | —O—CH₂—CH₂—CH(OCH₃)(CH₃) | $n_D^{32}$: 1.5696 |
| 91 | 6-Cl | S | CH₃ | —O—CH₂—CH₂—O—(phenyl) | m.p. 75–76 |
| 92 | 6-Cl | S | CH₃ | —O—CH₂—(phenyl) | |
| 93 | 6-Cl | S | CH₃ | —O—CH₂—CH₂—O—(phenyl with H₃C and Cl) | $n_D^{26}$: 1.6030 |
| 94 | 6-Cl | S | CH₃ | —O—CH₂—CH(O)CH₂ (epoxide) | |
| 95 | 6-Cl | S | CH₃ | —O—CH₂—CH₂—(phenyl) | |
| 96 | 6-Cl | S | CH₃ | —O—CH₂—CH₂—N(CH₃)₂ | |
| 97 | 6-Cl | S | CH₃ | —OH | |
| 98 | 5,6-Di—Cl | S | CH₃ | —O—CH₃ | |
| 99 | 5,6-Di—Cl | S | CH₃ | —O—CH₂—CH(CH₃)₂ | |
| 100 | H | O | CH₃ | —O—CH₃ | |
| 101 | H | O | CH₃ | —O—C₂H₅ | $n_D^{30}$: 1.5425 |
| 102 | H | O | CH₃ | —O—CH₂—CH₂—OCH₃ | |
| 103 | 5-CH₃ | O | CH₃ | —OCH₃ | m.p. 42–45 |
| 104 | 6-CH₃ | O | CH₃ | —OC₂H₅ | |
| 105 | 5-Cl | O | CH₃ | —OCH₃ | m.p. 76 |
| 106 | 5-Cl | O | CH₃ | —OC₂H₅ | m.p. 49–51 |
| 107 | 5-Cl | O | CH₃ | —O—C₃H₇ | $n_D^{27}$: 1.5559 |

-continued structure: R-(benzoxazole with A)-O-C6H4-O-CH(R1)-C(=O)-Y

| Example No. | R | A | $R_1$ | Y | m.p./b.p. (° C)/$n_D$ |
|---|---|---|---|---|---|
| 108 | 5-Cl | O | $CH_3$ | $-O-C_3H_7(i)$ | $n_D^{27}$:1.5395 |
| 109 | 5-Cl | O | $CH_3$ | $-O-CH_2-CH(CH_3)_2$ | $n_D^{27}$:1.5455 |
| 110 | 5-Cl | O | $CH_3$ | $-O-C_6H_{13}(n)$ | |
| 111 | 5-Cl | O | $CH_3$ | $-O-CH_2-CH(C_2H_5)-C_4H_9(n)$ | |
| 112 | 5-Cl | O | $CH_3$ | $-O-C_6H_{11}$ (cyclohexyl) | $n_D^{26.5}$: 1.5574 |
| 113 | 5-Cl | O | $CH_3$ | $-OH$ | |
| 114 | 5-Cl | O | $CH_3$ | $-O-CH_2-CH_2-O-CH_3$ | m.p. 103–105 |
| 115 | 5-Cl | O | $CH_3$ | $-O-CH_2-CH_2-O-C_2H_5$ | |
| 116 | 5-Cl | O | $CH_3$ | $-O-CH_2-CH_2-O-C_4H_9(n)$ | |
| 117 | 5-Cl | O | $CH_3$ | $-O-(CH_2-CH_2-O)_2-C_2H_5$ | $n_D^{27}$: 1.5396 |
| 118 | 5-Cl | O | $CH_3$ | $-O-CH_2-CH_2-CH(OCH_3)-CH_3$ | |
| 119 | 5-Cl | O | $CH_3$ | $-O-CH_2-CH_2-O-C_6H_5$ | $n_D^{26}$: 1.5806 |
| 120 | 5-Cl | O | $CH_3$ | $-O-CH_2-CH_2-C_6H_5$ | |
| 121 | 5-Cl | O | $CH_3$ | $-O-CH_2-C_6H_5$ | |
| 122 | 5-Cl | O | $CH_3$ | $-O-CH_2-CH_2-Cl$ | $n_D^{27}$: 1.5455 |
| 123 | 5-Cl | O | $CH_3$ | $-O-CH_2-CH(Cl)-CH_3$ | |
| 124 | 5-Cl | O | $CH_3$ | $-O-CH_2-CH_2-CH_2-Cl$ | $n_D^{27}$: 1.5636 |
| 125 | 5-Cl | O | $CH_3$ | $-O-(CH_2)_6-Cl$ | $n_D^{27}$: 1.5452 |
| 126 | 5-Cl | O | $CH_3$ | $-O-CH_2-CH(Br)-CH_3$ | |
| 127 | 5-Cl | O | $CH_3$ | $-O-CH(CH_2-Cl)_2$ | $n_D^{27}$: 1.5506 |
| 128 | 5-Cl | O | $CH_3$ | $-O-C_6H_{10}Cl$ (chlorocyclohexyl) | $n_D^{26}$: 1.5530 |
| 129 | 5-Cl | O | $CH_3$ | $-O-CH_2-C\equiv CH$ | $n_D^{26}$:1.5708 |
| 130 | 5-Cl | O | $CH_3$ | $-O-CH(CH_3)-C\equiv CH$ | |
| 131 | 5-Cl | O | $CH_3$ | $-O-CH_2-CH=CH_2$ | $n_D^{27}$: 1.5546 |
| 132 | 5-Cl | O | $CH_3$ | $-O-CH_2-CH=CH-CH_3$ | |
| 133 | 5-Cl | O | $CH_3$ | $-O-CH_2-CH_2-S-CH_3$ | |
| 134 | 6-Cl | O | $CH_3$ | $-O-CH_3$ | m.p. 97 |
| 135 | 6-Cl | O | $CH_3$ | $-O-C_2H_5$ | m.p. 82.5–83.5 |
| 136 | 6-Cl | O | $CH_3$ | $-O-C_3H_7$ | |
| 137 | 6-Cl | O | $CH_3$ | $-O-C_3H_7(i)$ | |
| 138 | 6-Cl | O | $CH_3$ | $-O-CH_2-CH(CH_3)_2$ | m.p. 51.5–53.5 |
| 139 | 6-Cl | O | $CH_3$ | $-OH$ | |
| 140 | 6-Cl | O | $CH_3$ | $-O-C_4H_9(n)$ | |
| 141 | 6-Cl | O | $CH_3$ | $-O-CH_2-CH_2-Cl$ | m.p. 64 |
| 142 | 6-Cl | O | $CH_3$ | $-O-C_6H_{13}(n)$ | |
| 143 | 6-Cl | O | $CH_3$ | $-O-CH_2-CH(C_2H_5)-C_4H_9(n)$ | |
| 144 | 6-Cl | O | $CH_3$ | $-O-CH_2-CH(Cl)-CH_3$ | $n_D^{28}$: 1.5533 |
| 145 | 6-Cl | O | $CH_3$ | $-CH_2-CH_2-OCH_3$ | |
| 146 | 6-Cl | O | $CH_3$ | $-O-CH_2-CH_2-O-C_4H_9(n)$ | |
| 147 | 6-Cl | O | $CH_3$ | $-O-(CH_2-CH_2-O)_2-C_2H_5$ | $n_D^{27}$: 1.5344 |
| 148 | 6-Cl | O | $CH_3$ | $-O-CH_2-CH_2-CH(CH_3)(OCH_3)$ | |
| 149 | 6-Cl | O | $CH_3$ | $-O-CH_2-C_6H_5$ | |
| 150 | 6-Cl | O | $CH_3$ | $-O-CH_2-CH_2-O-C_6H_5$ | $n_D^{20}$: 1.5781 |
| 151 | 6-Cl | O | $CH_3$ | $-O-CH_2-CH_2-CH_2-Cl$ | |
| 152 | 6-Cl | O | $CH_3$ | $-O-CH_2-CH_2-CH_2-CH_2-Cl$ | |
| 153 | 6-Cl | O | $CH_3$ | $-O-(CH_2)_6-Cl$ | |

-continued

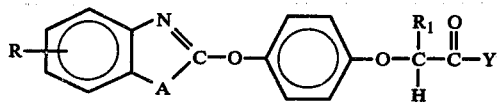

| Example No. | R | A | R₁ | Y | m.p./b.p. (° C)/n_D |
|---|---|---|---|---|---|
| 154 | 6-Cl | O | CH₃ | —O—CH(CH₂—Cl)₂ | m.p. 80–81.5 |
| 155 | 6-Cl | O | CH₃ | —O—(2-Cl-cyclohexyl) | |
| 156 | 6-Cl | O | CH₃ | —O—(cyclohexyl) | m.p. 91–93 |
| 157 | 6-Cl | O | H | —O—C₂H₅ | m.p. 95 |
| 158 | 5-Cl | O | H | —O—C₂H₅ | b.p.₀.₀₁: 195 |
| 159 | 6-Cl | S | H | —O—C₂H₅ | m.p. 86 |
| 160 | H | NCH₃ | CH₃ | O—C₂H₅ | m.p. 86 |
| 160 | H | S | H | —O—C₂H₅ | b.p.₀.₀₀₈: 207 |
| 161 | H | NCH₃ | CH₃ | —O—C₂H₅ | b.p.₀.₅:225 |
| 162 | H | NCH₃ | CH₃ | —O—CH₂—CH₂—O—CH₃ | b.p.₀.₁: 235 |
| 163 | 6-Cl | S | CH₃ | —O—(phenyl) | |
| 164 | 6-Cl | S | CH₃ | —O—(4-Cl-phenyl) | |
| 165 | 5-Cl | S | CH₃ | —O—(3-Cl-phenyl) | |
| 166 | 6-Cl | O | CH₃ | —O—(2-Cl-phenyl) | |
| 167 | 5-Cl | S | CH₃ | —O—(3-CH₃-phenyl) | |
| 168 | 6-Cl | O | CH₃ | —S—C₂H₅ | |
| 169 | 5-Cl | O | CH₃ | —S—CH₂—CH₂—CH₃ | |
| 170 | 6-Cl | S | CH₃ | —S—C₂H₅ | |
| 171 | 6-Cl | S | CH₃ | —S—CH₂—(phenyl) | |
| 172 | 5-Cl | S | CH₃ | —S—(phenyl) | |
| 173 | 5-Cl | O | CH₃ | —S—(4-Cl-phenyl) | |
| 174 | 5-Cl | O | CH₃ | —NH₂ | |
| 175 | 5-Cl | O | CH₃ | —NH—CH₃ | |
| 176 | 6-Cl | O | CH₃ | —N(CH₃)₂ | |
| 177 | 6-Cl | S | CH₃ | —NH—(phenyl) | |
| 178 | 6-Cl | S | CH₃ | —NH—(4-Cl-phenyl) | |
| 179 | 6-Cl | S | CH₃ | —ONa | |
| 180 | 6-Cl | S | CH₃ | —OK | |
| 181 | 6-Cl | S | CH₃ | —O[HNH(CH₃)₂] | |
| 182 | 6-Cl | S | CH₃ | —O[HN(C₂H₄OH)₃] | |
| 183 | 5-Cl | S | CH₃ | —ONa | |
| 184 | 5-Cl | S | CH₃ | —OK | |
| 185 | 5-Cl | S | CH₃ | —O[HNH₂CH₃] | |
| 186 | 5-Cl | O | CH₃ | —ONa | |
| 187 | 5-Cl | O | CH₃ | —OK | |
| 188 | 5-Cl | O | CH₃ | —O[H N(C₂H₅)₃] | |
| 189 | 5-Cl | O | CH₃ | —O[H N(C₂H₄OH)₃] | |
| 190 | 6-Cl | O | CH₃ | —ONa | |
| 191 | 6-Cl | O | CH₃ | —OK | |
| 192 | 6-Cl | O | CH₃ | —O[H NH(CH₃)₂] | |
| 193 | 6-Cl | O | CH₃ | —O[H NH₂CH₃] | |
| 194 | 6-Cl | O | CH₃ | —O[H N(C₂H₄OH)₃] | |
| 195 | 6-Cl | S | CH₃ | —O[H NH₂C₂H₄OH] | |
| 196 | 5-Cl | S | CH₃ | —OH | |
| 197 | H | S | CH₃ | —OH | |
| 198 | 5,6-DiCl | S | CH₃ | —OH | |
| 199 | H | S | CH₃ | —ONa | |
| 200 | H | S | CH₃ | —OK | |
| 201 | H | S | CH₃ | —O[H NH(CH₃)₂] | |
| 202 | 6-Cl | S | CH₃ | —O—(cyclopentyl) | |

-continued

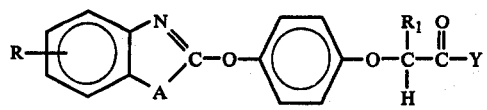

| Example No. | R | A | R₁ | Y | m.p./b.p. (° C)/$n_D$ |
|---|---|---|---|---|---|
| 203 | 5-Cl | S | CH₃ |  | |

In a manner analogous to Examples 2, 3, and 4 the following compounds were prepared:

R—[benzoxazole]—C(A)—O—[phenyl]—O—C(CH₃)(H)—CH₂—O—W

| Example No. | R | A | W | m.p./b.p. (° C)/$n_D$ |
|---|---|---|---|---|
| 204 | H | O | H | |
| 205 | 5-Cl | O | H | |
| 206 | 6-Cl | O | H | |
| 207 | 6-Cl | S | H | |
| 208 | 6-Br | S | H | |
| 209 | H | S | —C(O)—C₆H₅ | b.p.$_{0.05}$: 242 |
| 210 | 6-Cl | S | —C(O)—CH₃ | |
| 211 | 6-Cl | S | —C(O)—CH₂—Cl | |
| 212 | 5-Cl | S | —C(O)—CHCl₂ | |
| 213 | 5-Cl | S | —C(O)—cyclopropyl | |
| 214 | 5-Cl | O | —C(O)—CH₂—CH₂—CH₃ | |
| 215 | 5-Cl | O | —C(O)—C₆H₄—Cl | |
| 216 | 5-Cl | O | —C(O)—NHCH₃ | |
| 217 | 6-Cl | O | —C(O)—NH—C₂H₅ | |
| 218 | 6-Cl | O | —C(O)—NH—C₆H₅ | |

BIOLOGICAL EXAMPLES

EXAMPLE I: Pre-emergence treatment

Seeds of the annual weed grass Lolium were sown in pots and the surface of the soil was sprayed with wettable powder formulations according to the invention. The pots were then placed for 4 weeks in a greenhouse. The result of the treatment (as well as in the following examples) was evaluated according to the scheme of Bolle (cf. the following table).

The compounds according to the invention and specified in Table I exhibited a good action against Lolium. Some of the compounds were also effective against Echinochloa, Cynodon and Agropyron.

EXAMPLE II: Post-emergence treatment

Seeds of the weed grasses Lolium and Echinochloa were sown in pots and allowed to germinated in a greenhouse. 3 Weeks after sowing, the plants were sprayed with wettable powder formulations of the compounds according to the invention and the results were evaluated after 4 weeks.

The compounds of the invention specified in Tables IIa and IIb exhibited a good action against Lolium (IIa) and against Echinochloa (IIb).

EXAMPLE III: Crop plant tolerance

In further trials in the greenhouse seeds of a large variety of crop plants were sown in pots. Some of the pots were immediately treated (cf. Table IIIA. pre-emergence), while the other were placed in the greenhouse until the plants had developed 2 to 3 genuine leaves. They were then sprayed with the compounds of the invention (cf. Table III, B. post-emergence).

The results evaluated 4 to 5 weeks after application show that even in a concentration of 2.5 kg per hectare in pre-emergence and post-emergence application the compounds of the invention did no harm whatsoever or substantially no harm to dicotyledonous crop plants. Moreover, some of the substances did no damage to cultures of graminacea, such as barley, sorghum, maize, wheat and rice. Hence, the compounds of the invention are characterized by a highly selective action against the weed grasses specified in the preceeding examples.

TABLE

Evaluation scheme according to Bolle (Nachrichtenblatt des Deutschen Pflanzenschutzdienstes, 16, 1964, 92–94)

| Evaluation number | Damaging action in % on Weeds | | | Crops | |
|---|---|---|---|---|---|
| 1 | 100 | | | 0 | |
| 2 | 97.5 | to | <100 | >0 to | 2.5 |
| 3 | 95 | to | <97.5 | >2.5 to | 5 |
| 4 | 90 | to | <95 | >5 to | 10 |
| 5 | 85 | to | <90 | >10 to | 15 |
| 6 | 75 | to | <85 | >15 to | 25 |
| 7 | 65 | to | <75 | >25 to | 35 |
| 8 | 32.5 | to | <65 | >35 to | 67.5 |
| 9 | 0 | to | <32.5 | >67.5 to | 100 |

TABLE I

Herbicidal action with pre-emergence application in the greenhouse

| Ex. No. | kg/ha AS | effect against Lolium | Ex. No. | kg/ha AS | effect against Lolium |
|---|---|---|---|---|---|
| 135 | 2.5 | 1 | 106 | 2.5 | 4 |
| 1 | 2.5 | 1 | 40 | 2.5 | 3 |
| 2 | 2.5 | 1 | 58 | 2.5 | 1 |
| 6 | 2.5 | 1 | 105 | 2.5 | 4 |
| 134 | 2.5 | 2 | 57 | 2.5 | 1 |
| 53 | 2.5 | 2 | 23 | 2.5 | 3 |
| 25 | 2.5 | 1 | 59 | 3.0 | 1 |
| 60 | 3.0 | 1 | 61 | 3.0 | 1 |
| 62 | 3.0 | 1 | 65 | 3.0 | 1 |
| 66 | 3.0 | 1 | 67 | 3.0 | 1 |
| 71 | 3.0 | 1 | 68 | 3.0 | 1 |

TABLE I-continued

| | Herbicidal action with pre-emergence application in the greenhouse | | | | |
|---|---|---|---|---|---|
| Ex. No. | kg/ha AS | effect against Lolium | Ex. No. | kg/ha AS | effect against Lolium |
| 72 | 3.0 | 1 | 82 | 3.0 | 1 |
| 86 | 3.0 | 1 | 88 | 3.0 | 1 |
| 91 | 3.0 | 1 | 75 | 3.0 | 1 |
| 70 | 3.0 | 1 | 90 | 3.0 | 1 |
| 63 | 3.0 | 1 | 77 | 3.0 | 2 |
| 73 | 3.0 | 5 | 101 | 2.5 | 2 |
| 103 | 2.5 | 1 | 107 | 3.0 | 6 |
| 108 | 3.0 | 6 | 161 | 3.0 | 6 |
| 3 | 2.5 | 1 | 209 | 2.5 | 1 |

TABLE IIa

| | Herbicidal action with post-emergence application in the greenhouse (Lolium) | | | | |
|---|---|---|---|---|---|
| Ex. No. | kg/ha AS | effect against Lolium | Ex. No. | kg/ha AS | effect against Lolium |
| 135 | 2.5 | 1 | 1 | 2.5 | 1 |
| 58 | 2.5 | 1 | 57 | 2.5 | 1 |
| 25 | 2.5 | 1 | 59 | 3.0 | 1 |
| 60 | 3.0 | 1 | 61 | 3.0 | 1 |
| 62 | 3.0 | 1 | 65 | 3.0 | 1 |
| 66 | 3.0 | 1 | 67 | 3.0 | 1 |
| 71 | 3.0 | 1 | 68 | 3.0 | 1 |
| 72 | 3.0 | 1 | 82 | 3.0 | 1 |
| 86 | 3.0 | 1 | 88 | 3.0 | 1 |
| 91 | 3.0 | 1 | 75 | 3.0 | 1 |
| 70 | 3.0 | 3 | 90 | 3.0 | 1 |
| 63 | 3.0 | 1 | 77 | 3.0 | 1 |
| 78 | 3.0 | 4 | 73 | 3.0 | 1 |
| 103 | 2.5 | 1 | | | |

TABLE IIb

| Herbicidal effect with post-emergence application in the greenhouse (Echinochloa) | | |
|---|---|---|
| Example No. | kg/ha AS | effect against Echinochloa |
| 103 | 2.5 | 1 |
| 106 | 2.5 | 1 |
| 3 | 2.5 | 1 |
| 209 | 2.5 | 1 |
| 105 | 2.5 | 1 |
| 134 | 2.5 | 1 |
| 53 | 2.5 | 1 |
| 159 | 1.25 | 2 |
| 101 | 2.5 | 1 |

TABLE III

| | | | | | | crop plant tolerance | | | | | | | | |
|---|---|---|---|---|---|---|---|---|---|---|---|---|---|---|
| | | sugar beet | rape | cabbage | soja | kidney-bean | pea | cotton | tomatoe | tobaco | carrot | wheat | barley | rice |
| A. pre-emergence | kg/ha AS | | | | | | | | | | | | | |
| 1 | 2.5 | 2 | 2 | 1 | 1 | 3 | 2 | 1 | 1 | 1 | 3 | — | — | — |
| | 0.6 | 1 | 1 | 1 | 1 | 2 | 1 | 1 | 1 | 1 | 1 | — | — | — |
| 106 | 2.5 | 1 | 1 | 2 | 1 | 1 | 1 | 1 | 3 | 1 | 1 | 3 | 3 | — |
| | 0.6 | 1 | 1 | 1 | 1 | 1 | 1 | 1 | 2 | 1 | 1 | 2 | 2 | — |
| 135 | 2.5 | 2 | 1 | 1 | 1 | 2 | 1 | 1 | 1 | 1 | 1 | 2 | 2 | — |
| | 0.6 | 1 | 1 | 1 | 1 | 1 | 1 | 1 | 1 | 1 | 1 | 1 | 1 | — |
| B. post-emergence | | | | | | | | | | | | | | |
| 1 | 2.5 | 2 | 2 | 2 | 2 | 2 | 3 | 3 | 1 | 1 | — | — | — | — |
| | 0.6 | 1 | 1 | 1 | 1 | 1 | 1 | 1 | 1 | 1 | — | — | — | — |
| 106 | 2.5 | 2 | 1 | 1 | 4 | 4 | 3 | 2 | 1 | 1 | 1 | 3 | — | — |
| | 0.6 | 1 | 1 | 1 | 3 | 1 | 2 | 1 | 1 | 1 | 1 | 2 | — | — |
| 25 | 2.5 | 2 | 1 | 1 | 5 | 4 | 4 | 4 | 3 | 1 | 1 | 4 | — | 3 |
| | 0.6 | 1 | 1 | 1 | 4 | 2 | 2 | 2 | 1 | 1 | 1 | 3 | — | 2 |
| 135 | 2.5 | 2 | 1 | 1 | 1 | 1 | 1 | 1 | 1 | 1 | 1 | — | — | — |
| | 0.6 | 1 | 1 | 1 | 1 | 1 | 1 | 1 | 1 | 1 | 1 | — | — | — |

What is claimed is:

1. A compound of the formula

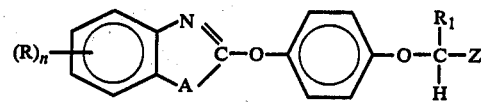

in which

R is halogen, $CF_3$, $NO_2$, CN, $C_1$–$C_4$alkyl, $C_1$–$C_4$ alkoxy or $C_1$–$C_4$alkylthio, A is O, S, NH, or N—($C_1$–$C_4$)alkyl, $R_1$ is H or $C_1$–$C_4$alkyl, Z is a group of the formula

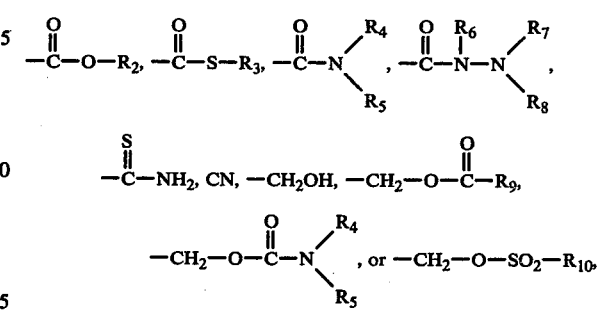

n is zero or 1 or 2, $R_2$ is H, $C_1$–$C_{12}$alkyl (optionally substituted by 1 to 6 halogen atoms), OH, $C_1$–$C_6$alkoxy, $C_1$–$C_4$alkylthio, $C_1$–$C_6$alkoxy-$C_2$–$C_6$alkoxy, halo-$C_1$–$C_2$alkoxy, methoxyethoxy-ethoxy, $C_1$–$C_4$alkylamino, di-$C_1$–$C_4$alkylamino, phenyl, oxiranyl and/or phenoxy which latter may be substituted once or twice by halogen or $C_1$–$C_4$alkyl; $C_5$–$C_6$cycloalkyl (optionally substituted by halogen or methyl); $C_3$–$C_6$alkenyl, halo-$C_3$–$C_6$-alkenyl or $C_5$–$C_6$cycloalkenyl, $C_3$–$C_4$alkinyl (optionally substituted once or twice by $C_1$–$C_6$alkyl, phenyl, halogen or $C_1$–$C_2$ alkoxy); phenyl (optionally substituted one to three times by $C_1$–$C_4$alkyl, $C_1$–$C_4$alkoxy, halogen, $NO_2$, or $CF_3$); furfuryl, tetrahydro-furfuryl, or the cation equivalent of an organic or inorganic base;

$R_3$ is $C_1$–$C_6$alkyl, phenyl-($C_1$–$C_2$)-alkyl, the phenyl radical optionally being substituted once or twice by $C_1$–$C_4$alkyl and/or halogen, $C_3$–$C_6$alkenyl, or phenyl (optionally substituted once or twice by $C_1$-$C_4$alkyl and/or halogen)

$R_4$ and $R_5$; which are identical or different, are H, $C_1$-$C_6$alkyl, hydroxy-($C_1$-$C_6$)-alkyl, $C_5$-$C_6$cycloalkyl, or phenyl (optionally substituted one to three times by $C_1$-$C_4$alkyl, $C_1$-$C_4$alkoxy, halogen, or $CF_3$), with the proviso that $R_4$ and $R_5$ cannot be phenyl at the same time; or wherein $R_4$ and $R_5$ together form a methylene chain having 2,4 or 5 $CH_2$-groups in which one $CH_2$ group may be replaced by O, NH, or $N(CH_3)$;

$R_6$ is H or $CH_3$, $R_7$ is H, $CH_3$, or $C_2H_5$, $R_8$ is H, $CH_3$, $C_3H_5$ or phenyl, $R_9$ is $C_1$-$C_6$alkyl (optionally substituted one to three times by halogen), cyclopropyl, $C_3$-$C_6$alkenyl, phenyl, $C_1$-$C_4$alkylphenyl $C_1$-$C_4$alkoxyphenyl, halophenyl, trifluoromethylphenyl or nitrophenyl and $R_{10}$ is $C_1$-$C_4$alkyl or phenyl (optionally substituted once or twice by halogen, $CF_3$, $NO_2$, or $C_1$-$C_4$alkyl).

2. 2-[4'-(5''-Chlorobenzoxazolyl-2''-oxy)-phenoxy]-propionic acid ($C_1$-$C_4$)alkyl esters.

3. 2-[4'-(6''-Chlorobenzoxazolyl-2''-oxy)-phenoxy]-propionic acid ($C_1$-$C_4$)alkyl esters.

4. 2-[4'-(6''-Chlorobenzthiazolyl-2''-oxy)-phenoxy]-propionic acid ($C_1$-$C_4$)alkyl esters.

5. 2-[4'-(6''-Bromobenzthiazolyl-2''-oxy)-phenoxy]-propionic acid ($C_1$-$C_4$)alkyl esters.

6. 2-[4'-(5''-Chlorobenzthiazolyl-2''-oxy)-phenoxy]-propionic acid ($C_1$-$C_4$)alkyl ester.

7. 2-[4'-(5''-Methylbenzthiazolyl-2''-oxy)-phenoxy]-propionic acid ($C_1$-$C_4$)alkyl esters.

8. 2-[4'-(benzthiazolyl-2''-oxy)-phenoxy]-propionic acid ($C_1$-$C_4$) alkyl esters, 9. 2-[4'-(Benzthiazolyl-2''-oxy)-phenoxy]-propanol 1.

10. 2-[4'-(5''-Chlorobenzoxazolyl-2''-oxy)-phenoxy]-propanol-1.

11. 2-[4'-(6''-Chlorobenzoxyzolyl-2''-oxy)-phenoxy]-propanol-1.

12. 2-[4'-(6''-Chlorobenzoxyzolyl-2''-oxy)-phenoxy]-propanol-1.

13. 2-[4'-(6''-Bromobenzthiazolyl-2''-oxy)-phenoxy]-propanol-1.

14. An herbicidal composition consisting essentially of an inert carrier and an herbicidally effective amount of a compound of the formula

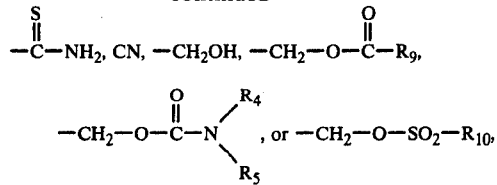

in which
R is halogen, $CF_3$, $NO_2$, CN, $C_1$-$C_4$alkyl, $C_1$-$C_4$alkoxy or $C_1$-$C_4$alkylthio,
A is O, S, NH, or N-($C_1$-$C_4$)alkyl,
$R_1$ is H or $C_1$-$C_4$alkyl,
Z is a group of the formula

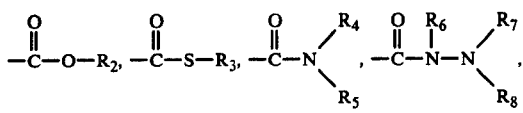

-continued

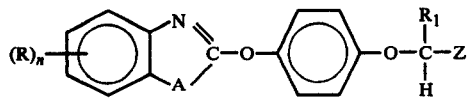

n is zero or 1 or 2, $R_2$ is H, $C_1$-$C_{12}$alkyl (optionally substituted by 1 to 6 halogen atoms, OH, $C_1$-$C_6$alkoxy, $C_1$-$C_4$alkylthio, $C_1$-$C_6$alkoxy-$C_2$-$C_6$alkoxy, halo-$C_1$-$C_2$alkoxy, methoxyethoxy-ethoxy, $C_1$-$C_4$alkylamino, di-$C_1$-$C_4$alkylamino, phenyl, oxiranyl and/or phenoxy which latter may be substituted once or twice by halogen or $C_1$-$C_4$alkyl); $C_5$-$C_6$cycloalkyl (optionally substituted by halogen or methyl); $C_3$-$C_6$alkenyl, halo-$C_3$-$C_6$alkenyl or $C_5$-$C_6$cycloalkenyl, $C_3$-$C_4$-alkinyl (optionally substituted once or twice by $C_1$-$C_6$alkyl, phenyl, halogen or $C_1$-$C_2$alkoxy); phenyl (optionally substituted one to three times by $C_1$-$C_4$alkyl, $C_1$-$C_4$alkoxy, halogen, $NO_2$, or $CF_3$); furfuryl, tetrahydrofurfuryl, or the cation equivalent of an organic or inorganic base;

$R_3$ is $C_1$-$C_6$alkyl, phenyl-($C_1$-$C_2$)-alkyl, the phenyl radical optionally being substituted once or twice by $C_1$-$C_4$alkyl and/or halogen, $C_3$-$C_6$alkenyl, or phenyl (optionally substituted once or twice by $C_1$-$C_4$alkyl and/or halogen), $R_4$ and $R_5$, which are identical or different, are H, $C_1$-$C_6$alkyl, hydroxy-($C_1$-$C_6$)-alkyl, $C_5$-$C_6$cycloalkyl, or phenyl (optionally substituted one to three times by $C_1$-$C_4$alkyl, $C_1$-$C_4$alkoxy, halogen or $CF_3$), with the proviso that $R_4$ and $R_5$ cannot be phenyl at the same time; or wherein $R_4$ and $R_5$ together form a methylene chain having 2, 4 or 5 $CH_2$-groups in which one $CH_2$ group may be replaced by O, NH, or $N(CH_3)$;

$R_6$ is H or $CH_3$, $R_7$ is H, $CH_3$, or $C_2H_5$, $R_8$ is H, $CH_3$, $C_2H_5$ or phenyl, $R_9$ is $C_1$-$C_6$alkyl (optionally substituted one to three times by halogen), cyclopropyl, $C_3$-$C_6$alkenyl, phenyl, $C_1$-$C_4$alkylphenyl $C_1$-$C_4$alkoxyphenyl, halophenyl, trifluoromethylphenyl or nitrophenyl and $R_{10}$ is $C_1$-$C_4$alkyl or phenyl (optionally substituted once or twice by halogen, $CF_3$, $NO_2$, or $C_1$-$C_4$alkyl).

15. A method for controlling the growth of undesired weed grasses which comprises treating the infested area with an herbicidally effective amount of a compound of the formula

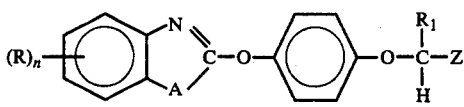

in which
R is halogen, $CF_3$, $NO_2$, CN, $C_1$-$C_4$alkyl, $C_1$-$C_4$alkoxy or $C_1$-$C_4$alkylthio,
A is O, S, NH, or N-($C_1$-$C_4$)alkyl,
R is H or $C_1$-$C_4$alkyl,
Z is a group of the formula $$-\overset{O}{\underset{\|}{C}}-O-R_2, \quad -\overset{O}{\underset{\|}{C}}-S-R_3, \quad -\overset{O}{\underset{\|}{C}}-N\overset{R_4}{\underset{R_5}{\diagdown}}, \quad -\overset{O}{\underset{\|}{C}}-\overset{R_6}{\underset{|}{N}}-N\overset{R_7}{\underset{R_8}{\diagdown}},$$

$$-\overset{S}{\underset{\|}{C}}-NH_2, \quad CN, \quad -CH_2OH, \quad -CH_2-O-\overset{O}{\underset{\|}{C}}-R_9,$$

$$-CH_2-O-\overset{O}{\underset{\|}{C}}-N\overset{R_4}{\underset{R_5}{\diagdown}}, \text{ or } -CH_2-O-SO_2-R_{10},$$

n is zero or 1 or 2, $R_2$ is H, $C_1$-$C_{12}$alkyl (optionally substituted by 1 to 6 halogen atoms), OH, $C_1$-$C_6$alkoxy, $C_1$-$C_4$alkylthio, $C_1$-$C_6$alkoxy-$C_2$-$C_6$-alkoxy, halo-$C_1$-$C_2$alkoxy, methoxyethoxy-ethoxy, $C_1$-$C_4$alkylamino, di-$C_1$-$C_4$alkylamino, phenyl, oxiranyl and/or phenoxy which latter may be substituted once or twice by halogen or $C_1$-$C_4$alkyl; $C_5$-$C_6$cycloalkyl (optionally substituted by halogen or methyl); $C_3$-$C_6$alkenyl, halo-$C_3$-$C_6$alkenyl or $C_5$-$C_6$cycloalkenyl, $C_3$-$C_4$alkinyl (optionally substituted once or twice by $C_1$-$C_6$alkyl, phenyl, halogen or $C_1$-$C_2$alkoxy); phenyl (optionally substituted one to three times by $C_1$-$C_4$alkyl, $C_1$-$C_4$alkoxy, halogen $NO_2$, or $CF_3$); furfuryl, tetrahydrofurfuryl, or the cation equivalent of an organic or inorganic base;

$R_3$ is $C_1$-$C_6$alkyl, phenyl-($C_1$-$C_2$)-alkyl, the phenyl radical optionally being substituted once or twice by $C_1$-$C_4$alkyl and/or halogen, $C_3$-$C_6$alkenyl, or phenyl (optionally substituted once or twice by $C_1$-$C_4$alkyl and/or halogen);

$R_4$ and $R_5$, which are identical or different, are H, $C_1$-$C_6$alkyl, hydroxy-($C_1$-$C_6$)-alkyl, $C_5$-$C_6$cycloalkyl, or phenyl (optionally substituted one to three times by $C_1$-$C_4$alkyl, $C_1$-$C_4$alkoxy, halogen or $CF_3$), with the proviso that $R_4$ and $R_5$ cannot be phenyl at the same time; or wherein $R_4$ and $R_5$ together form a methylene chain having 2, 4 or 5 $CH_2$-groups in which one $CH_2$ group may be replaced by O, NH, or $N(CH_3)$;

$R_6$ is H or $CH_3$, $R_7$ is H, $CH_3$, or $C_2H_5$, $R_8$ is H, $CH_3$, $C_3H_5$ or phenyl, $R_9$ is $C_1$-$C_6$alkyl (optionally substituted one to three times by halogen), cyclopropyl, $C_3$-$C_6$alkenyl, phenyl, $C_1$-$C_4$alkylphenyl $C_1$-$C_4$alkoxyphenyl, halophenyl, trifluoromethylphenyl or nitrophenyl and $R_{10}$ is $C_1$-$C_4$alkyl or phenyl (optionally substituted once or twice by halogen, $CF_3$, $NO_2$, or $C_1$-$C_4$alkyl).

* * * * *

UNITED STATES PATENT AND TRADEMARK OFFICE
CERTIFICATE OF CORRECTION

PATENT NO. : 4,130,413

DATED : December 19, 1978

INVENTOR(S) : Reinhard Handte et al.

It is certified that error appears in the above-identified patent and that said Letters Patent is hereby corrected as shown below:

Column 8, second last line of text above the table, after "5" insert --several of--.

Signed and Sealed this

Twenty-sixth Day of November 1985

[SEAL]

Attest:

Attesting Officer

DONALD J. QUIGG

Commissioner of Patents and Trademarks